(12) United States Patent
Liang et al.

(10) Patent No.: US 9,404,153 B2
(45) Date of Patent: Aug. 2, 2016

(54) DETECTION METHOD OF NUCLEIC ACID AND KIT AND USING THEREOF

(75) Inventors: Xingjie Liang, Beijing (CN); Hua Deng, Beijing (CN); Xiaowei Ma, Beijing (CN); Chan Li, Beijing (CN)

(73) Assignees: National Center for Nanoscience and Technology, Beijing (CN); Beijing Entry-Exit Inspection and Quarantine Bureau, Beijing (CN)

( * ) Notice: Subject to any disclaimer, the term of this patent is extended or adjusted under 35 U.S.C. 154(b) by 206 days.

(21) Appl. No.: 14/007,201

(22) PCT Filed: Apr. 12, 2011

(86) PCT No.: PCT/CN2011/072682
§ 371 (c)(1),
(2), (4) Date: Sep. 24, 2013

(87) PCT Pub. No.: WO2012/129821
PCT Pub. Date: Oct. 4, 2012

(65) Prior Publication Data
US 2014/0017671 A1    Jan. 16, 2014

(30) Foreign Application Priority Data
Mar. 30, 2011    (CN) .......................... 2011 1 0078665

(51) Int. Cl.
*C12Q 1/68* (2006.01)
(52) U.S. Cl.
CPC ................ *C12Q 1/686* (2013.01); *C12Q 1/689* (2013.01); *C12Q 1/6816* (2013.01)
(58) Field of Classification Search
None
See application file for complete search history.

(56) References Cited

U.S. PATENT DOCUMENTS

| | | | |
|---|---|---|---|
| 2003/0143604 A1 | 7/2003 | Storhoff et al. | |
| 2004/0110220 A1 | 6/2004 | Mirkin et al. | |

FOREIGN PATENT DOCUMENTS

| | | |
|---|---|---|
| CN | 1629305 A | 6/2005 |
| CN | 101768633 A | 7/2010 |
| EP | 2 143 805 A1 | 1/2010 |

OTHER PUBLICATIONS

Cao et al. (2006) Biosensors and Bioelectronics 22: 393-398.*
Liu et al. (2010) J. Mater. Chem.,20, 24-35.*
Stratagene (1988) catalog p. 35.*
Hao et al. (on line publication Jan. 2011) Biosensors and Bioelectronics vol. 26: 3398-3404.*
In re Sullivan CAFC 2007 decision.*
Ray et al., "A gold-nanoparticle-based fluorescence resonance energy transfer probe for multiplexed hybridation detection: accurate identification of bio-agents DNA," Nanotechnology 18 (2007) 375504 (6pp).
Qi et al., "Utilization of the rpoB Gene as a Specific Chromosomal Marker for Real-Time PCR Detection of Bacillus anthracis," Applied and Environmental Microbiology, Aug. 2001, vol. 67, No. 8, p. 3720-3727.
Klee et al., "Evaluation of different methods to discriminate Bacillus anthracis from other bacteria of the Bacillus cereus group," Journal of Applied Microbiology 100 (2006) 673-681.
Tang et al., "Visual DNA microarrays for simultaneous detection of human immunodeficiency virus type-1 and Treponema pallidum coupled with multiplex asymmetric polymerase chain reaction," Diagnostic Microbiology and Infectious Disease 65 (2009) 372-378.
Cao et al., "Nanoparticles with Raman Spectroscopic Fingerprints for DNA and RNA Detection," Science vol. 297, Aug. 30, 2002, p. 1536-1540.
Cai et al., "One-Pot Polymerase Chain Reaction with Gold Nanoparticles for Rapid and Ultrasensitive DNA Detection," Nano Res (2010) 3:557-563.
Mirkin et al., "A DNA-based method for rationally assembling nanoparticles into macroscopic materials," Nature vol. 382, Aug. 15, 1996, p. 607-609.
Li et al., "Label-Free Colorimetric Detection of Specific Sequences in Genomic DNA Amplified by the Polymerase Chain Reaction," J. Am. Chem. Soc. 2004, 126, 10958-10961.
Li et al., "Colorimetric detection of DNA sequences based on electrostatic interactions with unmodified gold nanoparticles," PNAS, Sep. 28, 2004, vol. 101, No. 39, 14036-14039.
Mehrabi et al., "Intercalating Gold Nanoparticles as Universal Labels for DNA Detection," Small 2007, 3, No. 9, 1491-1495.
M. Horisberger, "Colloidal Gold: A Cytochemical Marker for Light and Fluorescent Microscopy and for Transmission and Scanning Electron Microscopy," Scanning Electron Microscopy 1981 (pp. 9-31).
Elghanian et al., "Selective Colorimetric Detection of Polynucleotides Based on the Distance-Dependent Optical Properties of Gold Nanoparticles," Science, vol. 277, Aug. 22, 1997, p. 1078-1081.
Park et al., "Array-Based Electrical Detection of DNA with Nanoparticle Probes," Science vol. 295, Feb. 22, 2002, p. 1503-1506.
Zhang et al., "A multiplex nanoparticle-based bio-barcoded DNA sensor for the simultaneous detection of multiple pathogens," Biosensors and Bioelectronics 26 (2010) 1736-1742.
Hao et al., "DNA probe functionalized QCM biosensor based on gold nanoparticle amplification for Bacillus anthracis detection," Biosensors and Bioelectronics 26 (2011) 3398-3404.

(Continued)

*Primary Examiner* — Suchira Pande
(74) *Attorney, Agent, or Firm* — Volpe and Koenig, P.C.

(57) ABSTRACT

A detection method of nucleic acid is provided. The method includes: providing nucleic acid to be tested, making the nucleic acid to be tested react under asymmetric PCR conditions with a pair of primers for target nucleic acid amplification, DNA polymerase, adenine deoxyribonucleotide, guanine deoxyribonucleotide, cytosine deoxyribonucleotide and thymidine deoxyribonucleotide in a PCR buffer solution, mixing the reaction product and liquid that contains probe molecules, and judging whether the nucleic acid to be tested contains the target nucleic acid by observing the obtained mixture color or color change. A kit is also provided that can be used in the nucleic acid detection by the said method. Application of the method and the kit in inspection and quarantine is also provided. The method is a quick and easy, sensitive and a specific detection method of nucleic acid with direct observation using naked eyes. The method does not need additional equipment.

2 Claims, 2 Drawing Sheets

(56) References Cited

OTHER PUBLICATIONS

Tai et al., "Generation of a Specific Marker to Discriminate Bacillus anthracis from Other Bacteria of the Bacillus ereus Group," J. Microbiol. Biotechnol. (2007), 17(5), 806-811.

Chen et al., "Optical Detection of Human Papillomavirus Type 16 and Type 18 by Sequence Sandwich Hybridization With Oligonucleotide-Functionalized Au Nanoparticles," IEE Transaction on Nanobioscience, vol. 8, No. 2, Jun. 2009, p. 120-131.

Li et al., "Rolling Circle Amplification Combined with Gold Nanoparticle Aggregates for Highly Sensitive Identification of Single-Nucleotide Polymorphisms," Analytical Chemistry, vol. 82, No. 7, Apr. 1, 2010, p. 2811-2816.

S.K. Poddar, "Symmetric vs asymmetric PCR and molecular beacon probe in the detection of a target gene of adenovirus," Molecular and Cellular Probes (2000) 14, 25-32.

Luo et al., "Biosensor Using Gold Nanoparticle-Oligonucleotide DNA," J Prev Med Chin PLA, Apr. 2007, vol. 25, No. 2, p. 91-93 (English Abstract provided).

Guo et al., "Hybridization colouring method of detecting the products of HBV DNA ASY-PCR," J Fourth Mil Med Univ 1999, 20(9), p. 827-829 (English Abstract provided).

Gu et al., "Detection of Surface Plasmon Resonance on Microorganism's DNA with Asymmetric PCR Method," Space Medicine & Medical Engineering, vol. 23, No. 5, Oct. 2010, p. 319-323 (English Abstract provided).

Meng et al., "Detection of P53 Suppressor Gene Mutation in Pancreatic Neoplasm by Asymmetric PCR—Single Strand Conformation Polymorphisms," Acta Acad Med Nei Mongol, Sep. 2000, vol. 22, No. 3, p. 145-149 (English Abstract provided).

Zhang et al., "Enhancing the hybridization efficiency of oligomicroarray by asymmetric PCR," Acad J PLA Postgrad Med Sch Aug. 2005 26(4), p. 266-268 (English Abstract provided).

He et al., "Rapid colorimetric detection of methicillin resistant *Staphylococcus aureus* mecA gene by DNA-modified colloid gold nanoparticles probes," Chong Quig Medicine, vol. 39, No. 7, Apr. 2010, (4 pages).

\* cited by examiner

Tube 1    Tube 2    Tube 3

Tube 1    Tube 2

Tube 1    Tube 2

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial
<220> FEATURE:
<223> OTHER INFORMATION: The sequence is synthesized.

<400> SEQUENCE: 1
cgtaacaaga ggaaagagca                                                 20

<210> SEQ ID NO 2
<211> LENGTH: 20
<212> TYPE: DNA
<213> ORGANISM: Artificial
<220> FEATURE:
<223> OTHER INFORMATION: The sequence is synthesized.

<400> SEQUENCE: 2
ctgctactat tgtaggagga                                                 20

<210> SEQ ID NO 3
<211> LENGTH: 19
<212> TYPE: DNA
<213> ORGANISM: Artificial
<220> FEATURE:
<223> OTHER INFORMATION: The sequence is synthesized.

<400> SEQUENCE: 3
tcctccatct aggacagct                                                  19
```

<210> SEQ ID NO 4
<211> LENGTH: 20
<212> TYPE: DNA
<213> ORGANISM: Artificial
<220> FEATURE:
<223> OTHER INFORMATION: The sequence is synthesized.

<400> SEQUENCE: 4
aattcgattg cgataggagt                                           20

<210> SEQ ID NO 5
<211> LENGTH: 39
<212> TYPE: DNA
<213> ORGANISM: Artificial
<220> FEATURE:
<223> OTHER INFORMATION: The sequence is synthesized.

<400> SEQUENCE: 5
cttctctttg atgtcacgca tatggaatcc tgtggcatc                      39

<210> SEQ ID NO 6
<211> LENGTH: 19
<212> TYPE: DNA
<213> ORGANISM: Artificial
<220> FEATURE:
<223> OTHER INFORMATION: The sequence is synthesized.

<400> SEQUENCE: 6
gatgccacag gattccata                                            19

<210> SEQ ID NO 7
<211> LENGTH: 20
<212> TYPE: DNA
<213> ORGANISM: Artificial
<220> FEATURE:
<223> OTHER INFORMATION: The sequence is synthesized.

<400> SEQUENCE: 7
cttctctttg atgtcacgca                                           20

<210> SEQ ID NO 8
<211> LENGTH: 20
<212> TYPE: DNA
<213> ORGANISM: Artificial
<220> FEATURE:
<223> OTHER INFORMATION: The sequence is synthesized.

<400> SEQUENCE: 8
tgcgtgacat caaagagaag                                           20

<210> SEQ ID NO 9
<211> LENGTH: 19
<212> TYPE: DNA
<213> ORGANISM: Artificial
<220> FEATURE:
<223> OTHER INFORMATION: The sequence is synthesized.

<400> SEQUENCE: 9
gatgccacag gattccata                                            19

<210> SEQ ID NO 10
<211> LENGTH: 18
<212> TYPE: DNA
<213> ORGANISM: Artificial
<220> FEATURE:

```
<223> OTHER INFORMATION: The sequence is synthesized.

<400> SEQUENCE: 10
tggtgctctt tcctcttg                                              18

<210> SEQ ID NO 11
<211> LENGTH: 18
<212> TYPE: DNA
<213> ORGANISM: Artificial
<220> FEATURE:
<223> OTHER INFORMATION: The sequence is synthesized.

<400> SEQUENCE: 11
gtccgaatgc gattgatt                                              18

<210> SEQ ID NO 12
<211> LENGTH: 20
<212> TYPE: DNA
<213> ORGANISM: Artificial
<220> FEATURE:
<223> OTHER INFORMATION: The sequence is synthesized.

<400> SEQUENCE: 12
ggaaggcgct ttatgaccaa                                            20

<210> SEQ ID NO 13
<211> LENGTH: 20
<212> TYPE: DNA
<213> ORGANISM: Artificial
<220> FEATURE:
<223> OTHER INFORMATION: The sequence is synthesized.

<400> SEQUENCE: 13
aattaaagag cgcctttgga                                            20

<210> SEQ ID NO 14
<211> LENGTH: 28
<212> TYPE: DNA
<213> ORGANISM: Artificial
<220> FEATURE:
<223> OTHER INFORMATION: The sequence is synthesized.

<400> SEQUENCE: 14
tcaaactaat tgaggtggaa acatatcc                                   28

<210> SEQ ID NO 15
<211> LENGTH: 22
<212> TYPE: DNA
<213> ORGANISM: Artificial
<220> FEATURE:
<223> OTHER INFORMATION: The sequence is synthesized.

<400> SEQUENCE: 15
atgccaagag gacagagtga gt                                         22

<210> SEQ ID NO 16
<211> LENGTH: 20
<212> TYPE: DNA
<213> ORGANISM: Artificial
<220> FEATURE:
<223> OTHER INFORMATION: The sequence is synthesized.

<400> SEQUENCE: 16
ggaactcaga cgggatttgt                                            20
```

```
<210> SEQ ID NO 17
<211> LENGTH: 19
<212> TYPE: DNA
<213> ORGANISM: Artificial
<220> FEATURE:
<223> OTHER INFORMATION: The sequence is synthesized.

<400> SEQUENCE: 17
cctttatgat catgcaaga                                                  19
```

DETECTION METHOD OF NUCLEIC ACID AND KIT AND USING THEREOF

CROSS REFERENCE TO RELATED APPLICATION

This application is a 35 U.S.C. 371 national stage application of PCT/CN2011/072682, which was filed Apr. 12, 2011 and is incorporated by reference as if fully set forth.

TECHNICAL FIELD

The present invention relates to a detection method of nucleic acid, a kit for detection of nucleic acid applying the method, and use of the kit for inspection and quarantine.

BACKGROUND ART

Molecular diagnosis is a leading-edge technology in modern biological analysis and detection of specific nucleic acid sequence is an important part of biological analysis. Conventional molecular identification methods, such as fluorescent quantitative PCR (Qi Y. *Appl Environ Microbiol,* 2001, 67 (8): 3720-3727), RFLP (restriction fragment length polymorphism, S R Klee. *J. Applied Microbiology.* 2006, 100, 1364-5072), gene chip and sequencing, are complex and require large, expensive equipment and long time. They are very inaccessible for quick detection of some pathogenic microorganisms (biological weapons) like *Bacillus anthracis,* Therefore, the development of an alternative convenient, cheap, efficient, equipment-free analyzing means for the healthcare site use has very important practical significance.

Gold nano-particle (AuNP) is a colloidal bio-molecular marker with a diameter of 1-100 nm, enjoying advantages as good stability, small size effect, surface effect, quantum effects, optical effects, and unique biological affinity, widely used in the optics, electrics, and imaging (Horisberger M. *Scanning Electron Microscopy* II, 1981: 9-31). AuNP has a high extinction coefficient and its particle with a diameter of 13 nm has a sharp absorption peak at about 520 nm wavelength. Its self-assembled aggregation can significantly alter the absorption peak, and the surface plasmon resonance (SPR) can lead to a color change. Meanwhile, AuNP has a wide range of biological affinity coupling the DNA molecules and participating the self-assembly process, ultimately affecting physical properties of the AuNP solution (or colloidal gold solution), such as color and absorbance. Mirkin found self-assembly aggregation of the AuNP-DNA particles and color change in the colloidal solution caused by specific hybridization of DNA, first applying the AuNP to the biological detection (Mirkin C A. Nature, 1996, 382 (6592): 607-609). AuNP can couple thiol modified short chain DNA forming a detection probe, and when complementary same-length DNA exists in the solution, orderly and reversible agglomeration reaction occurs, developing two-dimensional, three-dimensional agglomeration structure in mesh and causing color change from ruby red to purple blue (Elghanian R. Science, 1997, 277 (22): 1078-1081). This naked-eye visible effect of AuNp forebodes a quick, easy way in biodetection. ssDNA (single stranded DNA) and dsDNA (double stranded DNA) are different in absorption of the AuNP, with the former to the negatively charged surface of AuNP making it in a stable state free from electrolyte salt ions' aggregation effect (Li H. *PNAS,* 2004, 101 (39): 14036-14039), Li accordingly designed nucleic acid hybridization colorimetric detection on the basis of the AuNP aggregation reaction. A conventional PCR is conducted against the target genes of the cardiac arrhythmias obtaining a double-stranded product. Then colloidal gold solution and the probes are added, after denaturation annealing, the colloidal gold solution turns from ruby red to purple blue if specific target nucleic acid has been amplified, if not, ruby red persists (Li H J, *Am Chem Soc.,* 216: 10958-10961, 2004). This new idea for nucleic acid detection is a non-crosslinked manner not requiring covalent modification of the AuNP and probe. However, in the actual operation, the ratio of the probe and the PCR product is uneasy to control, requiring large amount of pretest or purification and quantitative determination of the analytes of unknown concentration, so this method is unacceptable for application.

Recently, the combination of AuNP's SPR effect and the PCR produces a Nano-PCR detection method. Cai used an oligonucleotide probe coupled AuNP to supersede the conventional primer, amplifying exon sequence of HIV gp140 using PCR followed by colorimetric detection by the naked eyes. Although it is quick and easy (Miao Cai. *Nano Res.* 2010, 3: 557-563), the color change is not significant, limiting its applicability.

The above-mentioned calls for a simple and easy nucleic acid detection method with obvious color change.

SUMMARY OF THE INVENTION

Aiming to overcome the defects of the prior art, the present invention provides a simple, rapid, naked-eye visible nucleic acid detection method with significant color change, a kit depending on the method, and the application of the method and the kit in the inspection and quarantine.

The inventors of the present invention found that the insignificance of color change in the current available AuNP in the nucleic acid detection methods is largely blamed on poor binding between the probe and the nucleic acid to be detected, which results in a low AuNP SPR effect of the probe. Although many ways can be used to enhance the binding, few is acceptable due to complexity of the ways themselves, let alone groping and optimization of the detection systems themselves each time upon determination.

The inventors of the present invention found that the use of asymmetric PCR instead of the conventional PCR can obtain ssDNA-rich analyte nucleic acid and increase efficiency of hybridization between the probe and the analyte nucleic acid, further enhancing AuNP SPR effect in the probe and the color change as well.

The present invention provides a detection method of nucleic acid, wherein the method comprises contacting a pair of primer, DNA polymerase, triphosphate adenine deoxynucleotide, triphosphate guanine deoxynucleotide, triphosphate cytosine deoxynucleotide, and triphosphate thymidine nucleotide to the analyte nucleic acid under asymmetric PCR reaction conditions in a PCR buffer solution, mixing the post-contact product with probe-containing solution, and judging whether the analyte nucleic acid contain the target nucleic acid by observing the color or color change of the generated mixture.

The present invention also provides a kit for the above detection method of nucleic acid wherein the kit comprises: (1) a pair of primers capable of amplifying a target nucleic acid, the pair of primers comprise the upstream primer and downstream primer with a molar ratio meeting asymmetric PCR reaction requirements, the pair of primers are independently stored or deposited in the form of a mixture; (2) the said probe-containing solution independently stored from the said pair of primers or mixture thereof.

Further, the present invention also covers the use of the above-mentioned method or kit for the inspection and quarantine.

It is carried out as following when detecting genomic DNA fragment of *Bacillus anthracis* using the method according to the present invention: first, use the analyte nucleic acid as a template conducting asymmetric PCR, then mix the asymmetric PCR product with the probe hybridization solution containing the specific DNA fragment of genome of the *Bacillus anthracis*; and the color will change significantly within 2 minutes, but no color change occurs if the fragment does not exist. It is indicated that the present invention is a quick and easy, sensitive and specific, equipment-free and naked eyes visible nucleic acid detection method. A case indicating high sensitivity and simple nature of this method is that for 50 μL asymmetric PCR reaction with 0.01 ng of template nucleic acid, on the condition of taking 5 μL of asymmetric PCR product and mixing with 5 μL of probe solution at a probe concentration of 1.5 μM, significant color change can develop. The method can also be applied to detection of DNA fragment of mouse β-actin and *Vibrio cholerae*, indicating a certain degree of universality of this method.

DETAILED DESCRIPTION OF THE INVENTION

Figure 1:
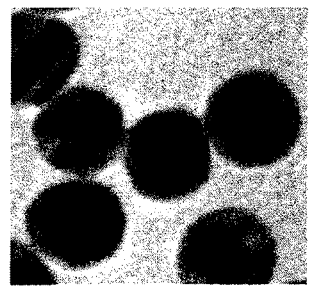
FIG. 1 is a TEM figure of the AuNP particles used by an embodiment of the present invention.

The present invention provides a nucleic acid detection method, wherein the method comprises contacting a pair of primer, DNA polymerase, triphosphate adenine deoxynucleotide, triphosphate guanine deoxynucleotide, triphosphate cytosine deoxynucleotide, and triphosphate thymidine nucleotide to the analyte nucleic acid under asymmetric PCR reaction conditions in a PCR buffer solution; mixing the post-contact product with probe-containing solution; and judging whether the analyte nucleic acid contain the target nucleic acid by observing the color or color change of the generated mixture.

The said analyte nucleic acid can be any nucleic acid sample, for example, nucleic acid sample extracted from the specimens; nucleic acid sample obtained from PCR amplification, or artificially obtained synthetic nucleic acid sample.

According to the present invention, said asymmetric PCR is a well-known method in the art, producing large amount of single strand DNA with a pair of primers of unequal amount in the PCR amplification. The pair of primers comprises non-limiting primer and limiting primer. The early stage of the PCR reaction predominantly produces double strand DNA and after depletion of the limiting primer (low concentration primer), the PCR led by non-limiting primer (the primer with high concentration) will produce large amounts of ssDNA. The key point of asymmetric PCR is to control the absolute amount of the limiting primer. The present invention follows the conventional concept of the non-limiting primer and limiting primer wherein the non-limiting primer and limiting primer are capable of amplifying the target nucleic acid.

According to the present invention, the reaction conditions of asymmetric PCR are conventional conditions in the art, however, variable depending on the analyte nucleic acid. Presence of the target nucleic acid is in question upon detection thus the asymmetric PCR may occur or not. The same asymmetric PCR should be conducted regardless of whether the analyte nucleic acid contains the target nucleic acid. Therefore, it should be noted that, the asymmetric PCR or conventional PCR conducted is not necessarily able to achieve the amplification, even though the added components and the reaction conditions are in compliance with the requirements of the asymmetric PCR, or the entire system has undergone the reaction process of the asymmetric PCR or conventional PCR.

According to the present invention, the asymmetric PCR reaction conditions include: the pre-denaturation temperature may be 90-98° C., the denaturation temperature may be 90-98° C., the annealing temperature may be 40-60° C., extension temperature can be 70-75° C., number of cycles is preferably greater than 10, more preferably 30-40; the molar ratio between limiting primer and non-limiting primer varies depending on the target nucleic acid only if it meets asymmetric PCR requirements, preferably, 1:5-240, more preferably, 1:10-100. Specific sequences of the limiting primer and non-limiting primer can be chosen using widely accepted method and the target nucleic acid can be designed and optimized using biology software such as Primer Premier, Oligo or DNAMAN.

According to the present invention, components added in an asymmetric PCR reaction can be the same with the currently available, wherein the PCR buffer solution is what corresponds to that used in DNA polymerase reaction. In general, The PCR buffer solution is supplied as a gift in the commercial product, and the amount added to the PCR buffer solution depends on concentration of the gift buffer. Usually the amount of buffer solution added is 5-50% of the post-contact product amount. For instance, if the gift PCR buffer is of 2×PCR buffer solution, the amount added is 50% of the post-contact product solution. The pH of the PCR buffer solution is preferably 8.5-9.5, more preferably 8.5-8.8. The added amount of the analyte nucleic acid varies within a relatively broad range, 0.001-1000 nM, only if it is enough for subsequent mixture with the probe solution and sustains significant color change. According to the present invention, the analyte nucleic acid may be a short synthetic fragment, PCR amplification product, or long genomic DNA, if the analyte nucleic acid is a short synthetic fragment or PCR amplification product, preferably a final concentration of the analyte nucleic acid is 0.01-10 nM, and if the analyte nucleic acid is genomic DNA, preferably a final concentration of the analyte nucleic acid is 10-300 nM, further preferably 0.01-300 nM. If weighed by mass, given 50 μl of the asymmetric PCR reaction system, the analyte nucleic acid to be added is preferably 10 pg-1 μg, and more preferably 0.1 ng-100 ng. The kind and amount of DNA polymerase added can be the same the currently available method, i.e., a final concentration of 0.01-0.2 U/μL, preferably 0.02-0.03 U/μL. The Promega PCR Master mix (2×) amplification system used by the present invention has a polymerase final concentration of 0.025 U/μL. Usually, the addition amount of the triphosphate adenine deoxynucleotide, triphosphate guanine deoxynucleotide, triphosphate cytosine deoxynucleotide, and triphosphate thymidine nucleotide (i.e., 4×dNTP) is in conventional range, e.g. 50-500 μM, more preferably 100-300 μM, in the present invention, the final concentration of dNTP is 200 μM. Under the above circumstance, total amount of the primers sustaining the target nucleic acid is for the present invention is preferably 0.1-10 μM, more preferably 0.3-3 μM.

According to the present invention, mixture of the post-contact product with the probe solution is preferably conducted in the presence of an inorganic salt MX, wherein M is Na and/or K, X is Cl, Br or I, one or more, the MX is preferably NaCl, and preferably, the inorganic salt MX added can achieve a final concentration of MX at 0.5-1M, and most preferably 0.8-1M. Inventors of the present invention found that NaCl of the above-described concentration range enables the detection system to develop very significant color change. According to the present invention, possibility of MX in the PCR buffer solution requires inclusion of MX in the buffer when calculating total concentration of the MX. However, the MX in the PCR buffer solution is very low, especially when only take a part of the asymmetric PCR product to mix with the probe solution. Thus the MX in the PCR buffer can be omitted. MX here involved is predominantly added when conducting mixture or the MX can be mixed with the probe solution in advance.

According to the present invention, condition for mixing the post-contact product and probe solution is far from rigid, the temperature should not be less than 10° C. because too low temperature can significantly lower molecular Brownian motion, not conducive to the hybridization. The upper limit of the temperature is lower than the Tm value of the hybridizing sequences, in general, the mixture temperature may be 15-55° C., preferably 20-50° C., most preferably at room temperature, i.e. 22-25° C.; the duration for mixing the post-contact product and probe solution can be 1-60 minutes, preferably 3-10 minutes. The technicians in this art are aware that the duration of mixture is the shortest time that produces the color change, and longer duration may cause more significant color change.

According to the present invention, given the mixture amount, the probe concentration in the probe solution is preferably 500-1500 nM, more preferably 600-1000 nM, for long-term storage, higher concentration is recommended in the stock solution, i.e., 2-4 μM.

According to the present invention, the probe molecule in the probe solution may include a plurality of conjugates, each formed by a kind of nano-particle and one or more oligonucleotides. At least part of the oligonucleotide nucleotide can be complementary to part of one chain of the target nucleic acid, preferably, at least part of two oligonucleotide is complementary to part of the same strand of the target nucleic acid; the oligonucleotide can be fully complementary to part of the target nucleic acid, or part of the oligonucleotide is complementary to part of the target nucleic acid, and the other part is not complementary. For example, part close to the nano-particles in the oligonucleotide is not complementary to the target nucleic acid, and the part far away the particles are complementary, and the complementary degree is based on stability of the hybrid. The essence of the invention is to improve the ability of binding between the probe and the target nucleic acid, thereby enhancing the SPR effect in the gold nano-particles on the probe, therefore, complement occurring far away from the nano-particles portion is to enhance binding capacity between the probe with the target nucleic acid, and the non-complement is to avoid decrease of SPR effect of the particles due to steric hindrance or rigidness of the oligonucleotide. Under guidance of the present invention, the technicians in the art can adjust or alter the probe/oligonucleotide sequence and the binding method to well realize this invention. These should be regarded as in the scope of the present invention.

The conjugate is product produced by binding the nano-particles with oligonucleotides. The concept of coupling is well known in the art, i.e., an organic reaction in which two chemical entities (or units) combine to generate one molecule, and the coupling method can be a well known one in the art, for instance, when the nano-particle is AuNP, 5' end of the oligonucleotide can be mercapto-modified (C6 on the 5' end base), and allow to contact the AuNP forming stable Au—S bond. The 5' end mercapto-modification can be achieved by conventional synthetic methods in this art, such as solid phase synthesis using a DNA synthesizer or obtained commercially.

According to the present invention, the probe molecule can be two conjugates or a plurality of conjugates; one conjugate may contain one nano-particle and one oligonucleotide; or may contain one nano-particles and a plurality of oligonucleotides, preferably, said probe in the probe-containing solution comprises two conjugates, each conjugate is formed by one nano-particle and one oligonucleotide. The two conjugates, with a molar ratio of 1:0.8-1.2, have the same nano-particles and different oligonucleotides. The same process and same feeding amount render the same concentration of the two conjugates. Thus in practical application, mixture of the two conjugates with the same amount render the molar ratio to comply with the above required. A precise molar ratio can be obtained by measuring absorbance at 260 nm or 520 nm. The present invention meets the above required at 1:1 by measuring the absorbance.

According to the present invention, the length of the oligonucleotide is not particularly limited, preferably, 10-50 nucleotides, more preferably 15-25 nucleotides, with which the optimal coupling efficiency can be achieved. Principle for designing the oligonucleotide probes: at the 3' end of the oligonucleotide preferably does not contain a plurality of C or G without potential of self-complement or hairpin structure formation.

A according to the present invention and under the above conditions, diameter of the nano-particles in the conjugate is not particularly limited, preferably, 5-100 nm, more preferably, 10-20 nm.

According to the essence of the present invention, any nano-particles apply to this invention only if they can produce color change by the change in spatial distance. Currently the preferably chose particle is the AuNP, and more preferably, with a diameter of about 13 nm in that: simple and stable preparation, little diameter difference, uniform morphology, good stability; sharp and narrow absorption peak at 520 nm, significant and naked-eyes visible color change of SPR effect in case of peak shift. However, the present invention is not limited to this very nano-particle. According to the present invention, the target nucleic acid can be nucleic acids or portion of the acids of any biological species. The detection of characteristic sequence portion of the nucleic acid helps to identify the owner of the analyte nucleic acid, in inspection and quarantine of harmful viruses and bacteria, the target nucleic acid can be at least one part of at least one genome of *Bacillus anthracis, Vibrio cholerae, Yersinia pestis, Bacillus* tularense, *Salmonella typhi, Brucella* species, variola virus, yellow fever virus, Eastern equine encephalitis virus, Western equine encephalitis virus, typhus group rickettsiae, botulinum toxin, the ornithosis *Chlamydia*, bottilinum toxin. staphylococcal enterotoxin, *Coccidioides immitis, Histoplasma*

*capsulatum*. Preferably, the target nucleic acid is at least part of the genome of the *Bacillus anthracis* or *Vibrio cholerae*. According to the essence of the present invention, the target nucleic acid of the present invention applies to many species in addition to the above ones. To verify the capability of the system, the inventors of the present invention selected a housekeeping gene, mice β-actin as an subject, because the housekeeping gene research is a widely accepted model in investigating of new system and the result is justifiable to other genes. In addition, it can be expected that simultaneous addition of many probes without knowing presence or absence of the harmful viruses or bacteria can confirm the presence if positive result occurs.

For example, the target nucleic acid sequence can be genomic DNA (or sequence fragments) of *Bacillus anthracis*, the limiting primer sequence can be SEQ ID NO: 1, and the non-limiting primer sequence can be SEQ ID NO: 2, the molar ratio between the limiting primer and the non-limiting primer is 1:10-100, and preferably, the ratio varies depending on the amplified target sequence, and for a specific target sequence, more preferably, the ratio can be obtained by a conventional test method. The probe consists of two conjugates formed by the gold nano-particles with oligonucleotides, the first conjugate is formed by AuNP and the oligonucleotide shown by SEQ ID NO: 3, while the second conjugate is formed by AuNP and the oligonucleotide shown by SEQ ID NO: 4; the molar ratio between is the first conjugate and the second conjugate is 1:0.8-1.2, more preferably 1:1.

According to the present invention, the detection method can be spectrophotometry and/or visual colorimetry, preferably, the visual colorimetry, which is easy and quick, without additional equipment. Conjugates unbound to the target nucleic acid has a maximum absorption peak at 524 nm, if bound, a red-shift, visually visible if larger than 7 nm, occurs due to the SPR effect. The red-shift for the present invention is at 575 nm for the mouse 3-actin and 537 nm for the genome DNA of *Bacillus anthracis*, both visually and easily visible. Usually, the significant color change occurs within 2-10 min, because the aggregation of the AuNP will reduce the intensity of the absorption peak due to lowered concentration of the monodisperse AuNP, making the solution color turns from the purple blue to transparent overnight or longer. At this time, the maximum absorption peak wavelength of the supernatant will change over time, the maximum absorption peak intensity will be further reduced, until undetectable.

It can be seen that in the early stage of the binding, the red-blue change is visible with naked eyes and over a long time the solution turning transparent is visible with naked eyes, i.e., as long as the analyte nucleic acid contains sufficient detectable amount of the target nucleic acid, the detection method of the present invention can provide clear visual result.

The present invention also provides a kit using the above method for detecting a nucleic, wherein the kit comprises:
(1) a pair of primers capable of amplifying the target nucleic acid, the pair of primers comprise the limiting primer and non-limiting primer, the molar ratio between the limiting primer and non-limiting primer meets the demand of the asymmetric PCR reaction, concretely, the molar ratio between the limiting primer and non-limiting primer is 1:5-240, more preferably 1:10-100; the primers are independently stored or deposited in the form of a mixture, preferably deposited in the form of a mixture; (2) the said probe-containing solution independently stored from the said pair of primers or mixture thereof.

Wherein, the amount of the respective components in the kit is adjustable according to the practical application.

According to the present invention, the kit does not necessarily include the DNA polymerase, PCR buffer solution and 4×dNTP because of their easy availability in the art and fastidious storage requirements. The components may present in the kit include: PCR buffer solution, DNA polymerase, triphosphate adenine deoxynucleotide, triphosphate guanine deoxynucleotide, triphosphate cytosine deoxynucleotide, and triphosphate thymidine nucleotide one or more, wherein, DNA polymerase is independently stored, preferably in a separate cryogenic ambiance; the rest are stored independently or in a mixture containing one or more components. The relative amounts of the above components and concentration can be the same as previously described.

The method and kit described in the present invention can be used in inspection and quarantine, especially venues requiring quick detection, such as railway stations, airports, customs and so on. The following embodiment gives detailed information of the present invention.

The method of the present invention is universally applicable and several representative target nucleic acids are detected, including the mouse β-actin gene, NCBI Genbank No. thereof is NM_007393.2; part of the mouse β-actin gene shown as SEQ ID NO: 5: 5'-CTT CTC TTT GAT GTC ACG CAT ATG GAA TCC the TGT GGC ATC-3'; specific sequence fragments of genomic DNA of *Bacillus anthracis*, NCBI Genbank No. thereof is AF_360750. 1; *Vibrio cholerae* CTX-A gene, NCBI Genbank No. thereof is EU_546136.1. The genomic DNA of *Bacillus anthracis* and *Vibrio cholerae* genomic DNA is gifted by the Academy of Military Medical Sciences.

Wherein the devices and reagents and conditions include: TECNAI G2 F30 TEM; trace UV-visible-fluorescence spectrophotometer e-SPECT; the oligonucleotide sequence (including conventional and 5' sulthydryl modified) is synthetised by Invitrogen; the Nap-5 purification column is purchased from GE; Promega DNA polymerase; PCR buffer supplied by Promega polymerase Promega PCR Mix (2×); condition for cloning mouse β-actin gene sequence and its fragments in the asymmetric PCR and conventional PCR: 94° C., 2 min; 94° C., 20 sec; 55° C., 20 sec; 70° C., 20 sec, 32 cycles, 70° C., 3 min; condition for cloning the anthrax sequence fragments of *Bacillus anthraci* in asymmetric PCR: 94° C., 3 min; 94° C.; 30 sec; 40° C., 30 sec; 72° C., 30 sec; 40 cycles, 72° C., 5 min; condition for cloning the *Vibrio cholerae* CTX-A in the asymmetric PCR: 94° C., 3 min; 94° C., 25 sec; 60° C., 20 sec; 72° C., 25 sec; 40 cycles; 72° C., 5 min; Using the Promega total RNA extraction kit from mouse liver separate mouse total RNA, obtaining cDNA by reverse transcription. The conventional chemical reagents involved by the present invention are of analytic grade and the nanograde water is processed by Milli-Q ultrapure water system of the Millipore Corporation, USA. Other operations comply with the reagent instructions and the "Molecular Cloning" (third edition).

Preparation Example 1

The present preparation is for synthesis of AuNP with a particle diameter of approximately 13 nm.

The AuNP is prepared using the classical chloroauric acid-sodium citrate reduction method. Soak all glass containers in aqua regia, rinse with nanoscale water, dry. In a 50 mL Erlenmeyer flask add 40 mL of nanoscale water and 0.4 mL of 1 g/mL HAuCl4 (chloroauric acid). Stir vigorously using a magnetic stirrer, heat to boiling. Then quickly add all at once 1.2 mL of 1 g/mL sodium citrate, allow the solution gradually change from light yellow to dark red, continue to heat for 15 minutes, then stop heating, continue to stir allowing to cool to room temperature. Keep the solution closed and stored at 4° C. free from light, use UV-visible spectrophotometer to measure the maximum absorption peak at 520 nm, the concentration is 3 nM. Drip 10 μL of the analyte onto the copper mesh, drain dry under vacuum, allow undergoing the TEM. The results are shown in FIG. 1, the AuNP diameter is approximately 13 nm, round, uniform, and of good monodisperse.

Preparation Example 2

According to cDNA sequence of mouse β-actin, choose the suitable hybrid sites and design the limiting primer P1 the non-limiting primer P2, oligonucleotide Oligo1 and Oligo2 for subsequent molecular hybridization, the sequences are as follows:

```
P1:
                                    (SEQ ID NO: 6)
5'-GAT GCC ACA GGA TTC CAT A-3';

P2:
                                    (SEQ ID NO: 7)
5'-CTT CTC TTT GAT GTC ACG CA-3';

Oligo1:
                                    (SEQ ID NO: 8)
5'-TGC GTG ACA TCA AAG AGA AG-3';

Oligo2:
                                    (SEQ ID NO: 9)
5'-GAT GCC ACA GGA TTC CAT A-3';
```

Wherein, C6 of the 5' end of the Oligo1 and Oligo2 for coupling are mercapto-modified. What mentionable is that the oligonucleotide probes used in the examples of the present invention are commercially available.

Preparation Example 3

The present preparation example is for the preparation of a liquid that contains the probe. Dissolve the 5OD mercapto modified oligonucleotides dry powder in 80 μL of the disulfide lysate (170 mM phosphate buffer, pH 8.0) obtaining a solution of oligonucleotide after complete solution. Divide the solution into four tubes, each containing 20 μL. Dissolve DTT (dithiothreitol) in disulfide lysate obtaining freshly prepared 0.1M DTT solution. Add 80 μL of the DTT solution to 20 μL of the oligonucleotide solution obtaining 100 μL DNA DTT reduction solution. Wrap it with aluminum foil and place at room temperature for 1 hour, vortex for 5 seconds every half hour. At the same time, with at least 10 mL above nano-grade water prewash the Nap-5 column. Feed the 100 μL DNA DTT reduction solution to the Nap-5 purification column, add 400 μL of Milli-Q water to wash the column, and finally add 500 μL of Milli-Q water to elute obtaining a mercapto group-containing oligonucleotide analyte. Collect the analytes in a 1.5 ml centrifuge tube, use the ultraviolet-visible spectrophotometer to conduct quantitative determination of OD260. At 9000×g, 4° C. centrifuge for 15 minutes, concentrate the AuNP to 17 nM, mix with the mercapto group-containing oligo nucleotides at a molar ratio of Au-NPS=200:1. Wrap the mixture with aluminum foil, shake at low-speed horizontally at room temperature for 16 hours or at 37° C. for 8 hours. Adjust the phosphoric acid buffer solution to a NaCl concentrations of 0.1M and the phosphate concentration of 10 mM (pH=7.0), and incubate for 40 hours at room temperature for continuous coupling. Centrifuge the resulting conjugate at 14000 rpm for 25-40 minutes, remove the supernatant; resuspend with phosphate buffer containing 0.1M NaCl, 10 mM phosphate in (pH=7.0) and centrifuge 3 times, wash and precipitate, sufficiently removing unbound ssDNA. Finally dissolve the conjugate in a phosphate buffer solution of 0.3M NaCl, 0.01% w sodium azide, 10 mM phosphate, (pH=7.0), store at 4° C. in the dark. Color of AuNP with normal function is ruby red without aggregation, the same as before the modification. According to the above method prepare the liquid containing the Probe1 and Probe2 corresponding to conjugate of Oligo1 and Oligo2 with AuNPs respectively (i.e., the mercapto-modified oligonucleotide powders are Oligo1 and Oligo2 powders respectively), given the amount of the liquid containing the probe as a reference, the Probe1 and Probe2 have a concentration of 1.5 μM.

Example 1

Conduct asymmetric PCR and establish a 50 μL asymmetric PCR reaction system, materials added is shown in Table 1.

TABLE 1

| Components | Final concentration |
| --- | --- |
| Template | 1 ng/μL |
| 4 × dNTP | 200 μM each |
| Promega PCR Mix | 1× |
| Promega DNA polymerase | 0.025 U/μL |
| P1 | 0.02 μM |
| P2 | 0.6 μM |
| ddH$_2$O | to 50 μL |

Wherein the template can be mouse cDNA; or a fragment of mouse cDNA such as the DNA of the SEQ ID NO: 5. The template used by this Example is DNA sequence shown in the SEQ ID NO: 5, commercially available.

Example 2

Conduct asymmetric PCR and materials added are shown in Table 2.

TABLE 2

| Components | Final concentration |
| --- | --- |
| Template | 1 ng/μL |
| 4 × dNTP | 200 μM each |
| Promega PCR Mix | 1× |
| Promega DNA polymerase | 0.025 U/μL |
| P1 | 0.01 μM |
| P2 | 0.6 μM |
| ddH$_2$O | to 50 μL |

Wherein the template used by this Example is DNA sequence shown in the SEQ ID NO: 5, Example 3

Conduct asymmetric PCR and materials added are shown in Table 3.

TABLE 3

| Components | Final concentration |
| --- | --- |
| Template | 1 ng/μL |
| 4 × dNTP | 200 μM each |

TABLE 3-continued

| Components | Final concentration |
|---|---|
| Promega PCR Mix | 1× |
| Promega DNA polymerase | 0.025 U/μL |
| P1 | 0.005 μM |
| P2 | 0.6 μM |
| ddH$_2$O | to 50 μL |

Wherein the template used by this Example is mouse cDNA.

Comparison Example 1

Conduct asymmetric PCR and materials added are shown in Table 4.

TABLE 4

| Components | Final concentration |
|---|---|
| Template | 0 |
| 4 × dNTP | 200 μM each |
| Promega PCR Mix | 1× |
| Promega DNA polymerase | 0.025 U/μL |
| P1 | 0.02 μM |
| P2 | 0.6 μM |
| ddH$_2$O | to 50 μL |

Wherein the asymmetric PCR system is not added with the template acting as a negative control.

Comparison Example 2

Conduct conventional PCR and materials added are shown in Table 5.

TABLE 5

| Components | Final concentration |
|---|---|
| Template | 1 ng/μL |
| 4 × dNTP | 200 μM each |
| Promega PCR Mix | 1× |
| Promega DNA polymerase | 0.025 U/μL |
| P1 | 0.2 μM |
| P2 | 0.2 μM |
| ddH$_2$O | to 50 μL |

Wherein the template is DNA sequence of SEQ ID NO: 5.

Comparison Example 3

Conduct asymmetric PCR and materials added are shown in Table 6.

TABLE 6

| Components | Final concentration |
|---|---|
| Template | 1 ng/μL |
| 4 × dNTP | 200 μM each |
| Promega PCR Mix | 1× |
| Promega DNA polymerase | 0.025 U/μL |
| P1 | 0.6 μM |
| P2 | 0.02 μM |
| ddH$_2$O | to 50 μL |

Wherein the template is DNA sequence of SEQ ID NO: 5.

Examples 4-5

Conduct asymmetric PCR reaction, in accordance with the method described in the Example 1 except that the final concentrations of the P1 added are 0.0025 μM and 0.006 μM respectively.

Examples 6-10

Conduct asymmetric PCR reaction, in accordance with the method described in the Example 1 except that the final concentrations of the template added are 2 ng/μL, 0.2 ng/μL, 0.02 ng/μL, 0.002 ng/μL 0.0002 ng/μL respectively.

Test Example 1

Figure 2:
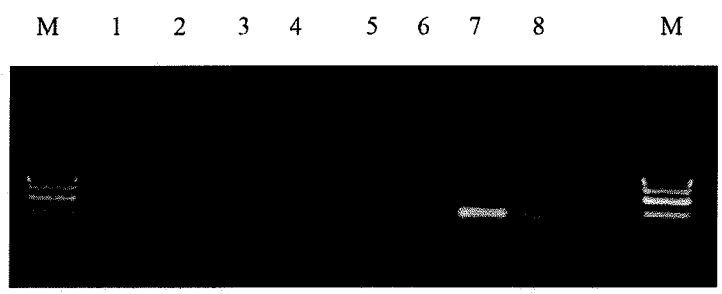
FIG. 2 is a figure of agarose gel electrophoresis of the asymmetric PCR product in an embodiment of the present invention.

From the products of the Examples 1-5 and the products of the comparison examples 1-3 take 5 μL each to conduct agarose gel electrophoresis, the result is shown in FIG. 2., wherein, lane M is the marker, and the bands from bottom to top label 50 bp, 100 bp, 150 bp, 200 bp, 300 bp, 400 bp and 500 bp respectively; lanes 1-5 are products of the Examples 1-5, lane 6 is a negative control without the template, i.e. the product of the comparison example 1, lane 7 is the control of the conventional PCR, i.e. product of comparison example 2, lane 8 is the control using P1 as the limiting primer and P2 as non-limiting primer, i.e., the asymmetric PCR product of comparison example 3.

Test Example 2

Figure 3:
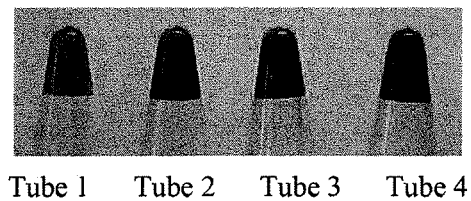
FIG. 3 is color change after mixture of asymmetric PCR product with the probe solution in an embodiment of the present invention.

Take 5 μL each from the product of the Example and the product of the comparison examples 1-3, and take 10 μL from the preparation example 3 that contains the probe, mix with 4 μL of 4M NaCl solution at room temperature (25° C.) for 2 minutes, observe and photograph, the result is shown in FIG. 3, wherein the tubes 1-4 respectively correspond to the Example 3 and the comparison examples 1-3. Determine the absorption peak wavelength and absorbance of the products. The absorption peak wavelength and absorbance of the products of the Example 3 and the comparison examples 1-3 are (575 nm, 1.52), (524 nm, 0.74), (524 nm, 0.69), (524 nm, 0.79) respectively.

Test Example 3

Figure 4:
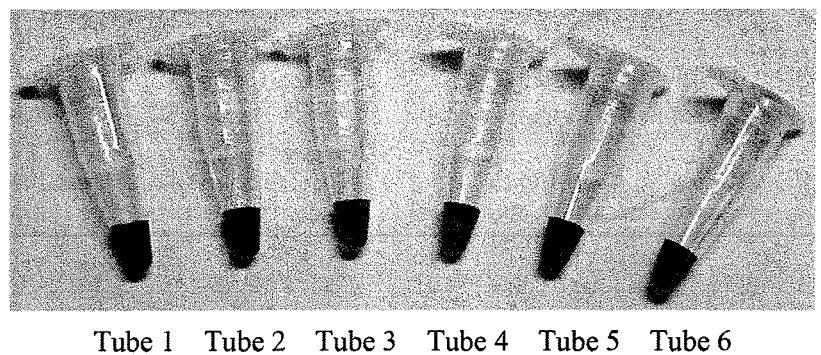
FIG. 4 is result of sensitivity appraisal in an embodiment of the present invention.

Take 5 μL each from the product of the Examples 6-10 and the product of the comparison example 1, and take 10 μL from the preparation example 3 that contains the probe, mix with 4 μL of 4M NaCl solution at room temperature (25° C.) for 10 minutes, observe and photograph, the result is shown in FIG. 4, wherein the tubes 1-6 respectively correspond to the Example 6-10 and the comparison examples 1. Determine the absorption peak wavelength and absorbance of the products. The absorption peak wavelength and absorbance of the products of the Examples 6-10 are (575 nm, 1.63), (575 nm, 1.51), (575 nm, 1.39), (575 nm, 1.26), (575 nm, 0.92).

Test Example 4

Figure 5:
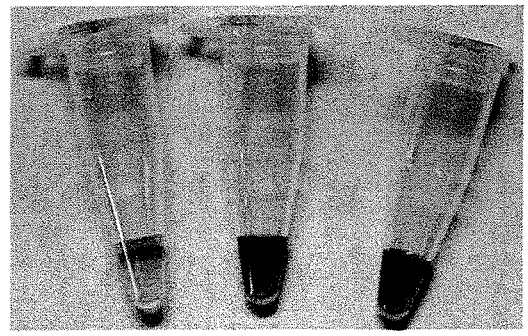
FIG. 5 is result of specificity appraisal in an embodiment of the present invention.

Take 5 μL each from the product of the Examples 1-2 and the product of the comparison example 1 and 3, and take 10 μL from the preparation example 3 that contains the probe, mix with 4 μL of 4M NaCl solution at room temperature (25° C.) for 2 minutes, observe and photograph, the result is shown in FIG. 5, wherein the tubes 1-3 respectively correspond to the Example 1 and the comparison examples 1 and 3. Determine the absorption peak wavelength and absorbance of the products.

The absorption peak wavelength and absorbance of the products of the Examples 1-2 and 4-5 are (575 nm, 1.59), (575 nm, 1.56), (575 nm, 1.43) and (575 nm, 1.40).

Preparation Example 4

According to the genomic DNA sequence fragments of the *Bacillus anthracis*, select appropriate hybridization sites and design the limiting primer P3, non-limiting primer the P4 and the oligonucleotide Oligo3 and Oligo4 for subsequent molecular hybridization. The squences are as follows:

```
P3:
                                     (SEQ ID NO: 1)
5'-CGT AAC AAG AGG AAA GAG CA-3';

P4:
                                     (SEQ ID NO: 2)
5'-CTG CTA CTA TTG TAG GAG GA-3';

Oligo3:
                                     (SEQ ID NO: 3)
5'-T CCT CCA TCT AGG ACA GCT-3';

Oligo4:
                                     (SEQ ID NO: 4)
5'-AA TTC GAT TGC GAT AGG AGT-3'.
```

Preparation Example 5

In accordance with the method described in Preparation Example 3 prepare solutions containing Probe3 and Probe4. The Probe3 and Probe4 are conjugates of the Oligo3 Oligo4 respectively. Based on the amount of the liquid containing the probe, the concentrations of the above Probe3 and Probe4 are equally 1.9 µM.

Example 11

Conduct asymmetric PCR and establish a 50 µL asymmetric PCR reaction system, materials added is shown in Table 7.

TABLE 7

| Components | Final concentration |
| --- | --- |
| Template | 1 ng/µL |
| 4 × dNTP | 200 µM each |
| Promega PCR Mix | 1× |
| Promega DNA polymerase | 0.025 U/µL |
| P3 | 0.05 µM |
| P4 | 2.5 µM |
| ddH$_2$O | to 50 µL |

Wherein the template may be of the genomic DNA of the *Bacillus anthracis*; or a special part of the gene sequence of the *Bacillus anthracis*; the template in the Example is genomic DNA of the *Bacillus anthracis*.

Examples 12-15

Conduct asymmetric PCR and establish a 50 µL asymmetric PCR reaction system, materials added is shown in Table 8.

TABLE 8

| | Final concentration | | | |
| --- | --- | --- | --- | --- |
| Components | Example 12 | Example 13 | Example 14 | Example 15 |
| Template | 2 ng/µL | 0.2 ng/µL | 0.02 ng/µL | 0.002 ng/µL |
| 4 × dNTP | | 200 µM each | | |
| Promega PCR Mix | | 1× | | |
| Promega DNA polymerase | | 0.025 U/µL | | |
| P3 | | 0.05 µM | | |
| P4 | | 2.5 µM | | |
| ddH$_2$O | | to 50 µL | | |

Wherein the template is DNA genome of *Bacillus anthracis*.

Test Example 5

Figure 6:
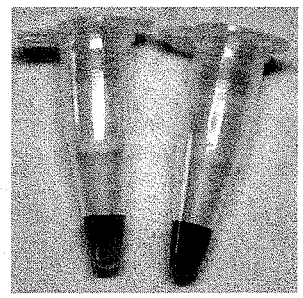
FIG. 6 is color change after mixture of asymmetric PCR product with the probe solution in another embodiment of the present invention.
Figure 7:
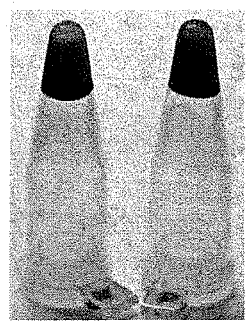
FIG. 7 is a color change after mixture of asymmetric PCR product with the probe solution in a further embodiment of the present invention.

Take 5 µL each from the product of the Examples 11-15 and the product of the comparison example 1, and take 10 µL from the preparation example 5 that contains the probe, mix with 4 µL of 4M NaCl solution at room temperature (25° C.) for 2 minutes, observe and photograph, the result is shown in FIG. 6, wherein the tubes 1 and 2 respectively correspond to the Example 11 and the comparison example 1. Determine the absorption peak wavelength and absorbance of the products. The absorption peak wavelength and absorbance of the products of the Examples 11-15 are (537 nm, 2.97), (537 nm, 3.27), (537 nm, 2.91), (537 nm, 2.79) and (537 nm, 2.53).

Preparation Example 6

According to the genomic DNA sequence fragments of the *Bacillus anthracis*, select appropriate hybridization sites and design the non-limiting primer P5, limiting primer P6 and the oligonucleotide Oligo5 and Oligo6 for subsequent molecular hybridization. The sequences are as follows:

```
P5:
                                    (SEQ ID NO: 10)
5'-TGG TGC TCT TTC CTC TTG-3';

P6:
                                    (SEQ ID NO: 11)
5'-GTC CGA ATG CGA TTG ATT-3';

Oligo5:
                                    (SEQ ID NO: 12)
5'-GGA AGG CGC TTT ATG ACC AA-3';

Oligo6:
                                    (SEQ ID NO: 13)
5'-AAT TAA AGA GCG CCT TTG GA-3'.
```

Preparation Example 7

In accordance with the method described in Preparation Example 3 solutions containing Probe5 and Probe6 are prepared. The Probe5 and Probe6 are conjugates of the Oligo5 and Oligo6 respectively. Based on the amount of the liquid containing the probe, the concentrations of the above Probe3 and Probe4 are equally 1.4M.

Example 16

Conduct asymmetric PCR and establish a 50 µL asymmetric PCR reaction system, materials added is shown in Table 9.

TABLE 9

| Components | Final concentration |
| --- | --- |
| Template | 1 ng/μL |
| 4 × dNTP | 200 μM each |
| Promega PCR Mix | 1× |
| Promega DNA polymerase | 0.025 U/μL |
| P5 | 2.5 μM |
| P6 | 0.05 μM |
| ddH$_2$O | to 50 μL |

Wherein the template is DNA genome of *Bacillus anthracis*.

Examples 17-20

Conduct asymmetric PCR and materials added are shown in Table 10.

TABLE 10

| | Final concentration | | | |
|---|---|---|---|---|
| Components | Example 17 | Example 18 | Example 19 | Example 20 |
| Template | 2 ng/μL | 0.2 ng/μL | 0.02 ng/μL | 0.002 ng/μL |
| 4 × dNTP | 200 μM each | | | |
| Promega PCR Mix | 1× | | | |
| Promega DNA polymerase | 0.025 U/μL | | | |
| P5 | 2.5 μM | | | |
| P6 | 0.05 μM | | | |
| $ddH_2O$ | to 50 μL | | | |

Wherein said template DNA genome of *Bacillus anthracis*.

Test Example 6

Take 5 μL each from the product of the Examples 16-20, and take 10 μL from the preparation example 7 that contains the probe, mix with 4 μL of 4M NaCl solution at room temperature (25° C.) for 2 minutes, Determine the absorption peak wavelength and absorbance of the products. The absorption peak wavelength and absorbance of the products of the Examples 16-20 are (537 nm, 2.92), (537 nm, 3.11), (537 nm, 2.83), (537 nm, 2.66) and (537 nm, 2.51).

Preparation Example 8

According to the *Vibrio cholerae* CTX-A gene sequence, select appropriate hybridization sites and design the non-limiting primer P7, limiting primer P8 and the oligonucleotide Oligo5 and Oligo6 for subsequent molecular hybridization. The sequences are as follows:

```
P7:
                                        (SEQ ID NO: 14)
5'-TCA AAC TAA TTG AGG TGG AAA CAT ATC C-3';

P8:
                                        (SEQ ID NO: 15)
5'-ATG CCA AGA GGA CAG AGT GAG T-3';

Oligo7:
                                        (SEQ ID NO: 16)
5'-GGA ACT CAG ACG GGA TTT GT-3';

Oligo8:
                                        (SEQ ID NO: 17)
5'-CCT TTA TGA TCA TGC AAG A-3'.
```

Preparation Example 9

In accordance with the method described in preparation example 3 prepare solutions containing Probe7 and Probe8. The Probe7 and Probe8 are conjugates of the Oligo7 Oligo8 respectively. Based on the amount of the liquid containing the probe, the concentrations of the above Probe7 and Probe8 are equally 1 μM.

Example 21

Conduct asymmetric PCR and materials added are shown in Table 11.

TABLE 11

| Components | Final concentration |
|---|---|
| Template | 1 ng/μL, |
| 4 × dNTP | 200 μM each |
| Promega PCR Mix | 1× |
| Promega DNA polymerase | 0.025 U/μL |
| P7 | 0.6 μM |
| P8 | 0.02 μM |
| $ddH_2O$ | to 50 μL |

Wherein the template can be genomic DNA of *Vibrio cholerae* or DNA fragment of the CTX-A of the *Vibrio cholerae*, the template in the Example is the genomic DNA of the *Vibrio cholerae*.

Examples 22-25

Conduct asymmetric PCR and materials added are shown in Table 12.

TABLE 12

| | Final concentration | | | |
|---|---|---|---|---|
| Components | Example 22 | Example 23 | Example 24 | Example 25 |
| template | 2 ng/μL | 0.2 ng/μL | 0.02 ng/μL | 0.002 ng/μL |
| 4 × dNTP | 200 μM each | | | |
| Promega PCR Mix | 1× | | | |
| Promega DNA polymerase | 0.025 U/μL | | | |
| P7 | 0.6 μM | | | |
| P8 | 0.02 μM | | | |
| $ddH_2O$ | to 50 μL | | | |

Wherein the template is genome DNA of the *Vibrio cholerae*.

Test Example 7

Take 5 μL each from the product of the Examples 21-25, and take 10 μL from the preparation example 7 that contains the probe, mix with 4 μL of 4M NaCl solution at room temperature (25° C.) for 2 minutes, observe and photograph, the result is shown in FIG. 7, wherein the tubes 1 and 2 respectively correspond to the Example 21 and the comparison example 1. Determine the absorption peak wavelength and absorbance of the products. The absorption peak wavelength and absorbance of the products of the Examples 21-25 are (537 nm, 2.77), (537 nm, 2.91), (537 nm, 2.76), (537 nm, 2.33) and (537 nm, 2.18).

FIG. 1 indicates the AuNP obtained according to the preparation example 1 is uniform and has a good monodispersibility.

FIG. 2 indicates that the Examples 1-5 can obtain asymmetric PCR product containing certain amount of ssDNA, correct in position compared to the Marker without non-specific bands; in the negative control of the comparison example 1, i.e. the lane 6 does not show any band; in the conventional PCR, i.e., lane 7, very clear bands appear, lagging behind those of the Examples 1-5; in the comparison example 3 that obtains the complementary single strand, i.e., the lane 8, clear bands are visible, with the same position as in the Examples 1-5. These indicate good specificity and stability enjoyed by the method of the present invention.

FIG. 3 is of the test of product of the Example 3, showing significant color change within 2 minutes as shown in tube 1. The UV-visible spectrophotometer at 575 nm found an absorption peak with an intensity of 1.52; while tubes 2-4 corresponding to the comparison examples 1-3 do not give color change. These are completely consistent with the actual situation, i.e., product of the Example 3 really contains the target nucleic acid being able to give color change, while the comparison examples 1-3 do not contain the target nucleic acid (may contain dual chain or antisense target nucleic acid), being unable to give color change. These indicate that the method of the present invention is very reliable; On the other hand, although the electrophoresis results show that the content of the target nucleic acid in the Example 3 (i.e., lane 3, FIG. 2) is not high compared to the comparison example 1 (lane 1) and comparison example 2 (i.e., lane 2), the Example 3 still gives significant color change in the detection, indicating high sensitivity of the method of the present invention.

FIG. 4 shows template sensitivity test results resulting from a 10-fold serial dilution of the template followed by an asymmetric PCR. The mixture of products of the Examples 6-10 with the probe-containing solution shows significant color change within 2-5 minutes as well as an absorption peak at 575 nm with an intensity of 0.92-1.63, while the control tube 6 in the comparison example 1 does not give significant color change even after overnight. The above indicates the nucleic acid detection method of the present invention is rapid, sensitive and reliable.

FIG. 5 shows specificity in that only the target nucleic acid-containing product of the Example 1 gives color change, not for the template-free comparison example 1 or for the comparison example 3 that has obtained the complementary sequence of the target nucleic acid, indicating high specificity enjoyed by the method of the present invention.

FIG. 6 shows result of test example 5 against a sequence fragment of the genomic DNA of the *Bacillus anthracis*, indicating all asymmetric PCR products give significantly positive results regardless of template concentration. This reveals that the method of the present invention has a very good sensitivity and stability for detecting sequence fragment of the genomic DNA of the *Bacillus anthracis*.

Test example 6 is against another sequence fragment of the genomic DNA of the *Bacillus anthracis*. Similarly, all asymmetric PCR products give significantly positive results regardless of template concentration at 537 nm with an intensity of 2.51-3.11. This indicates the present invention is universally applicable.

FIG. 7 shows result of test example 7 against a DNA sequence fragment of *Vibrio cholerae* CTX-A gene, indicating all asymmetric PCR products give significantly positive results, naked eye visible, regardless of template concentration at 537 nm with an absorption peak intensity of 2.18-2.91. This further demonstrates the method of the present invention is rapid, sensitive, reliable, and universally applicable.

What is claimed is:

1. A kit for the detection of *Bacillus anthracis* genomic DNA target nucleic acid, wherein the kit comprises:
   (1) a pair of primers capable of amplifying the target nucleic acid, the pair of primers comprising a limiting primer and a non-limiting primer, the molar ratio between the limiting primer and the non-limiting primer meets the demand of an asymmetric PCR reaction, and the pair of primers are stored independently or in a mixture, wherein the limiting primer sequence consists of the sequence of SEQ ID NO: 1, the non-limiting primer sequence consists of the sequence of SEQ ID NO: 2, and the molar ratio between the limiting primer and the non-limiting primer is 1:10-100; and
   (2) a probe-containing solution independently stored from the pair of primers or mixture thereof, wherein a probe in the probe-containing solution comprising two conjugates, a first conjugate of the two conjugates comprises a first gold nano-particle having a diameter of 5-100 nm and an oligonucleotide with a sequence consisting of the sequence of SEQ ID NO: 3, a second conjugate of the two conjugates comprises a second gold nano-particle having a diameter of 5-100 nm and an oligonucleotide with a sequence consisting of the sequence of SEQ ID NO: 4, the molar ratio between the first conjugate and the second conjugate is 1:0.8-1.2, and the first gold nano-particle and the second gold nano-particle are identical.

2. The kit according to claim 1, wherein said kit further comprises one or more of PCR buffer solution, DNA polymerase, triphosphate adenine deoxynucleotide, triphosphate guanine deoxynucleotide, triphosphate cytosine deoxynucleotide, and triphosphate thymidine nucleotide, wherein, DNA polymerase is independently stored, and the rest is stored independently or in mixture containing one or more components.

* * * * *